(12) United States Patent
Marche et al.

(10) Patent No.: US 8,998,874 B2
(45) Date of Patent: Apr. 7, 2015

(54) RESILIENT LAMINATE AND REINFORCED NON-WOVEN FABRIC

(75) Inventors: Thierry Marche, La Chapelle Basse Mer (FR); Nathalie Moinard, Nantes (FR)

(73) Assignee: Aplix, Paris (FR)

( * ) Notice: Subject to any disclaimer, the term of this patent is extended or adjusted under 35 U.S.C. 154(b) by 575 days.

(21) Appl. No.: 13/258,047

(22) PCT Filed: Mar. 5, 2010

(86) PCT No.: PCT/FR2010/000190
§ 371 (c)(1),
(2), (4) Date: Sep. 21, 2011

(87) PCT Pub. No.: WO2010/109087
PCT Pub. Date: Sep. 30, 2010

(65) Prior Publication Data
US 2012/0022490 A1    Jan. 26, 2012

(30) Foreign Application Priority Data
Mar. 23, 2009    (FR) ..................................... 09 01339

(51) Int. Cl.
| A61F 13/15 | (2006.01) |
| A61F 13/62 | (2006.01) |
| B32B 5/14 | (2006.01) |
| B32B 5/26 | (2006.01) |
| B32B 7/12 | (2006.01) |
| B32B 25/14 | (2006.01) |
| A61F 13/00 | (2006.01) |
| A61F 13/02 | (2006.01) |
| A61F 13/49 | (2006.01) |

(52) U.S. Cl.
CPC ............. *B32B 5/14* (2013.01); *A61F 13/00038* (2013.01); *A61F 13/0269* (2013.01); *A61F 13/15593* (2013.01); *A61F 13/15756* (2013.01); *A61F 13/49015* (2013.01); *A61F 13/4902* (2013.01); *A61F 13/622* (2013.01); *A61F 2013/00127* (2013.01); *B32B 5/26* (2013.01); *B32B 7/12* (2013.01); *B32B 25/14* (2013.01); *Y10T 428/24017* (2013.01)

(58) Field of Classification Search
USPC .................. 604/391, 387, 386, 389, 394, 396
See application file for complete search history.

(56) References Cited

U.S. PATENT DOCUMENTS

| 6,195,850 B1 * | 3/2001 | Melbye et al. .................. 24/304 |
| 6,245,401 B1 | 6/2001 | Ying et al. |
| 2003/0109843 A1 | 6/2003 | Gibbs |
| 2005/0060849 A1 | 3/2005 | Vanbenschoten et al. |

FOREIGN PATENT DOCUMENTS

| WO | WO 01/53076 | 7/2001 |
| WO | WO 2009/042556 A1 | 4/2009 |

* cited by examiner

*Primary Examiner* — Jacquelin F. Stephens
(74) *Attorney, Agent, or Firm* — Renner, Kenner, Greive, Bobak, Taylor & Weber (57) ABSTRACT

Hook part of a self-gripping hook and loop closure, in particular for a nappy, comprising a hook element comprising a sheet from which hooks protrude and a laminated element fixed to the hook element, the laminate extending in a transverse direction between two respective left and right lateral edges, comprising a layer fixed to at least one layer (2, 3) of non-woven fabric by a layer of adhesive, in particular interposed between two layers of non-woven fabric by being fixed by one respective layer of adhesive to each layer of non-woven fabric, the layer being in one piece or an integral layer and comprising a resilient zone (6; 16) in the form of film, in particular made of an elastomeric material.

11 Claims, 7 Drawing Sheets

RESILIENT LAMINATE AND REINFORCED NON-WOVEN FABRIC

The present invention relates to a laminate comprising at least one resilient film fixed by adhesive to at least one layer of non-woven fabric, in particular two respective upper and lower layers of non-woven fabric. This type of laminate is used, in particular, in applications in the field of clothing, in particular disposable clothing, such as nappies and adult incontinence devices, or in the medical field, in the form of elastic bandages. In the case of nappies, said laminates are conventionally used in the parts forming the waistband around the waist of the baby. In the case of a particularly advantageous application for nappies, said laminates are used to produce the resilient flaps which ensure that the nappy is held firmly on the baby, in particular in a resilient manner, the flap forming a hook part, bearing for example male elements of a self-gripping closure, in particular hooks, intended to cooperate, for example, with loops of a central part of the waistband of the nappy.

Laminates of this type are already known in the prior art, in particular in the French patent application No. 05 11343 filed on 8 Nov. 2005 in the name of the applicant. The laminates which are disclosed therein are intended, in particular, to be fixed, on the one hand, to the structure of the nappy and, on the other hand, to a narrow strip comprising hooks. The non-woven fabrics forming these laminates of the prior art are either non-woven fabrics which do not have the capacity for expansion, or non-woven fabrics which may be stretched in one direction. In the case of non-expandable non-woven fabrics, for the laminate to have resilient capacities, it is necessary to "activate" it, in particular by partially breaking the fibres which form it or at least by reducing the cohesion thereof, in particular by breaking the fibres with cutters, to confer in this manner a resilience to the laminate as a whole.

A laminate is disclosed in U.S. Pat. No. 6,245,401 comprising a layer consisting of a resilient film and two films which are less resilient but permeable to water vapour, and a layer of non-woven fabric which may be used as the external covering of a nappy structure which is impermeable to liquids.

A laminate is disclosed in U.S. Pat. No. 5,773,374 comprising two layers of non-woven fabrics which sandwich a resilient element, said resilient element consisting of a core made of resilient material and two skins on both sides of the core which have been previously stretched and fixed in the stretched state to the core, which is itself in the stretched state, so that once fixed the skins shrink at the same time as the core to form corrugations. The element consisting of the core and the two skins is thus provided with resilience between its length at rest and its maximum length when it is stretched so that the skins no longer form corrugations. The method of manufacture of the laminate is thus complicated and time-consuming.

A laminate is disclosed in WO-A-01/53076 comprising two layers of non-woven fabrics sandwiching a layer in one piece made of a resilient material. Furthermore, a non-resilient reinforcing film is interposed between the resilient layer and a layer of non-woven material, with the interposition of glue on both sides of the reinforcing film to bond it, on the one hand, to the non-woven fabric and, on the other hand, to the resilient layer. This assembly by bonding a plurality of films has the result that the manufacturing method of the laminate is complicated and time-consuming.

From US 2005/0060849A1 it is known to co-extrude two strips, one made of an elastomeric material and the other made of a thermoplastic material into which hooks may be moulded, the co-extrusion being carried out on a support layer without the interposition of glue, and then by pulling the two co-extruded strips apart in the direction CD, subsequently to obtain separate hook elements.

In all cases, it is difficult either to produce the laminate, in particular because it consists of a large number of parts which makes it complex, or to ensure the fixing of the laminate at high speed either to the structure of the nappy or to the hook flap without using upper and lower non-woven fabrics which have higher grammages, which has a disadvantageous effect on mass production costs.

According to a further example of the prior art, it is known to treat zones of the non-woven fabric(s) to eliminate the resilient properties of the laminate in the region of these zones, for example by the addition of a complementary layer of rigid film or non-woven fabric increasing the thickness of the laminate. However, also in this case, the processing is costly and not suitable for implementing on rapid mass production lines.

The present invention aims to overcome the drawbacks of the prior art by proposing a laminate comprising at least one resilient film fixed by adhesive between two layers of non-woven fabric, which may be obtained in a very simple manner, particularly suitable for very large scale production and which at the same time is simpler to assemble to a nappy, and in particular to the structure of the nappy, and to which it is also easier to assemble an element of narrow width comprising hooks to form a hook part to permit the closure of said nappy.

According to the invention, a hook part of a self-gripping hook and loop closure, in particular for a nappy is as defined as in claim 1, improvements being defined in the sub-claims 2 to 9.

According to the invention, by the term "in one piece" is understood a layer which is formed by fixing together a plurality of parts, in particular films, using an intermediate fixing means, such as adhesive or glue. In particular, the layer in one piece is a layer obtained by extruding a material or by co-extruding a plurality of materials.

In particular, said one resilient zone in the form of film is in direct contact with at least one layer of non-woven fabric, with the possible interposition of just one adhesive layer, in particular glue.

Preferably, the laminate has a width measured in the transverse direction between the two left and right terminal edges, a thickness measured in the direction of the stack of layers of the laminate and a length in the direction perpendicular to the direction in width and the direction in thickness, the layers or sheets of the non-woven fabric and adhesive extending over the entire width of the laminate, whilst the total width of the zone(s) in the form of resilient film(s) is strictly less than the width of the laminate and the total width of the zone(s) in the form of reinforcing film(s) is also strictly less than the width of the laminate.

In particular, according to a preferred embodiment of the invention, the zone(s) in the form of reinforcing film(s) and the zone(s) in the form of resilient film(s), before the fixing thereof to the at least one layer of non-woven fabric, are formed in one piece or as a single film by co-extrusion so that their lateral edges come into mutual contact. The materials of the reinforcing films and of the resilient film(s), for example thermoplastic and elastomeric materials, are extruded adjacent to one another, so that the reinforcing films and the resilient film form a single piece.

Preferably, the zone(s) in the form of reinforcing films consist of a material made from a formulation or recipe incorporating, in particular, thermoplastic, possibly elastomeric, materials which, according to the method for testing elongation disclosed below, confers fewer properties of elongation at equivalent load than the zone(s) in the form of resilient films. Preferably, said zones are non-resilient.

With the hook part according to the invention, it is possible now to obtain, with a grammage which is equal to the non-woven fabrics used, an improved resistance to lateral traction and effective fixing of the hook part in the region of its edges to the structure of a nappy, or for a grammage which is lower than at least one of the non-woven fabrics used, in particular between 5 and 20 g/m², preferably between 5 and 15 g/m², in particular between 5 and 10 g/m², equally effective fixing as in the case of the hook parts of the prior art comprising non-woven fabrics of higher grammage.

According to a preferred embodiment, the hook sheet, consisting of a base strip and a plurality of hooking elements originating from the strip, is fixed, for example by bonding, hot-calendering, ultrasonic welding or the like, to one external face of the at least one non-woven fabric forming the laminate, in the region of the edge on one zone which is located above or below one of the reinforcing zones, in particular lateral zones.

According to a further embodiment, the hook sheet, consisting of a base strip and a plurality of hooking elements originating from the strip, is fixed for example by bonding, hot-calendering, ultrasonic welding or the like, to one external face of at least one of the lateral and/or central reinforcing zones.

According to a preferred embodiment of the invention, the two layers of adhesive, in particular of glue, respectively between each non-woven fabric and the layer in one piece or the integral layer consisting of at least two reinforcing zones in the form of film and at least one resilient zone in the form of film, are produced so that between the non-woven fabric and the part(s) forming a resilient zone of the intermediate layer, the adhesive is arranged in the form of strips separated from one another by strips without adhesive.

Either the non-woven fabric has a capacity for extension in the transverse direction, in which case the separated strips of glue make it possible to provide the laminate with a resilience, or the selected non-woven fabric is not extendable, and it is thus activated by stretching the assembly transversely so that the clusters of fibres of the non-woven fabric bind to the strips of glue, whilst between the strips of glue hollow parts are formed in the non-woven fabric, and after stretching, the non-woven fabric will have ridge shapes and hollow shapes and is able to be stretched.

Preferably, the thickness of the layer in one piece or integral layer comprising the reinforcing zone(s) in the form of film(s) and the resilient zone(s) in the form of film(s) is substantially uniform, in particular uniform in the region of the joints between the reinforcing zones and the resilient zones. In particular, in the region of the joints, the two zones each have at the joint region a thickness which is smaller than in the vicinity of the joint, the total thicknesses of the two zones in the form of films in the region of the joint being substantially equal to the thickness of one or other of the zones in the form of films in the vicinity of the joint.

According to a further embodiment, the joint between two resilient and reinforcing zones is formed along a bevelled interface.

Preferably, the total widths of the resilient zone(s) in the form of film(s) and of the reinforcing zone(s) in the form of film(s), including that of the central zone when it is provided, is substantially equal to the width of the laminate, so that the terminal reinforcing zones extend substantially exactly as far as the respective terminal edge of the laminate.

According to a further application which is also very advantageous, the widths of the resilient zone(s) in the form of film(s), and of the reinforcing zone(s) in the form of film(s) including that of the central zone when it is provided, are such that one of the two terminal reinforcing zones extends substantially exactly as far as the respective lateral edge whilst the other of the two terminal reinforcing zones extends beyond the respective lateral edge, so as to protrude beyond the laminate.

According to a further application which is very advantageous, the widths of the resilient zone(s) in the form of film(s) and of the reinforcing zone(s) in the form of film(s), including that of the central zone when it is provided, are such that one of the two terminal reinforcing zones extends substantially exactly as far as the respective lateral edge whilst the other of the two terminal reinforcing zones, extends on this side of the respective lateral edge thereof, so as to form an edge which only consists of a non-woven fabric or two non-woven fabrics and an intermediate layer of glue.

However, for each of the reinforcing zones in the form of film it may be conceived, independently of the other, that it extends either exactly as far as its respective lateral edge, or on the other side of this respective edge, or on this side of this respective edge.

The present invention also relates to a method for obtaining a hook part according to the invention as defined in claim 10.

Preferably, the co-extruded film consisting of the resilient film(s) and the reinforcing film(s) is made of one or more material(s) impermeable, in particular, to air and/or liquids.

According to a further feature of the invention, said invention relates to a nappy defining a front part, a rear part and a crotch part connecting the front part and the rear part, and two lateral intermediate parts connecting the upper left and right lateral edges of the rear part with the respective upper left and right lateral edges of the front part, each intermediate part being joined in a fixed manner, for example by welding, to one respective upper lateral edge of the rear part, and each intermediate part comprising a laminate extending in a transverse direction between two respective left and right lateral edges, comprising a layer fixed to at least one layer of non-woven fabric by a layer of adhesive, in particular interposed between two layers of non-woven fabric by being fixed respectively by one respective layer of adhesive to each layer of non-woven fabric, the layer being in one piece or an integral layer and comprising a resilient zone in the form of film, in particular made of an elastomeric material, characterised in that:
  the layer in one piece or integral layer comprises at least one terminal reinforcing zone in the form of film which extends from the resilient zone in the form of film towards one of the lateral edges;
  no resilient zone being located between said one of the lateral edges and the reinforcing zone in the form of film; and
  the at least one reinforcing zone in the form of film being less stretchable than said one resilient zone in the form of film, in particular being less resilient, and preferably being non-resilient, for example being made of a thermoplastic material.

According to an advantageous embodiment, at least one hook element comprising a base strip and hooks originating from the strip, is fixed to the laminate, a loop element is fixed to the front part and the arrangement is such that the nappy is closed around the waist of the wearer by the cooperation between the hooks of the intermediate part and the loops of the front part.

According to a further embodiment which is also advantageous, the intermediate parts are fixed to the front part in a non-detachable manner, for example by welding.

The present invention also relates to a nappy as defined in claim 11.

By way of example, an embodiment of the invention is now disclosed by referring to the drawings, in which.

Figure 1:
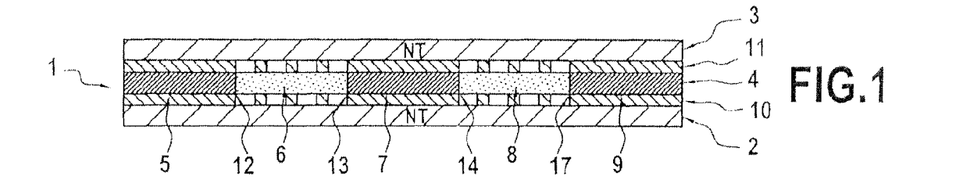
FIG. 1 shows a schematic cross-sectional view of an embodiment of a laminate according to the invention.

In FIG. 1 a laminate 1 comprising a first lower layer 2 of non-woven fabric and a second upper layer 3 of non-woven fabric is shown. Between these two lower and upper layers 2 and 3 of non-woven fabric (in the figures, the cross-sectional view is shown, given that the laminate in its entirety is an element of which the length is perpendicular to the plane of FIGS. 1 and 2), an intermediate layer 4 is formed. This intermediate layer 4 consists of a lateral left reinforcing film 5 made of thermoplastic material, a left resilient film 6 made of elastomeric material, a central reinforcing film 7 made of thermoplastic material, a right resilient film 8 made of elastomeric material and a right lateral reinforcing film 9 made of thermoplastic material.

The layers 10 and 11 of glue are interposed between each layer of non-woven fabric and the intermediate layer 4. The total width of the laminate is equal to the width of each non-woven fabric as well as the width of each layer of glue. The total widths of the three reinforcing films and the two resilient films is equal to the width of the laminate.

The two left and right reinforcing films extend as far as one respective left and right edge of the laminate. It is also possible to conceive that a small edge without a reinforcing strip is formed on each edge of the laminate (see FIG. 13) or that in contrast one or both films protrude beyond the respective edge (see FIG. 7, 8, 11 or 12). In all cases, one of the edges of the two terminal reinforcing films is the location of the points of assembly of the terminal reinforcing films which are the most remote from the resilient film(s).

Figure 21:
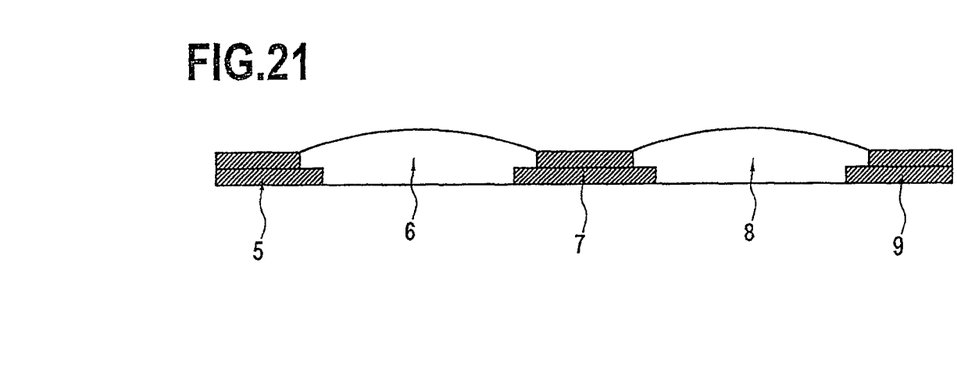
FIG. 21 shows a cross-sectional view of the layer of the embodiment of FIG. 1 after having been formed by extrusion and before being assembled to one or two layers of non-woven fabric.

As may be seen in FIG. 21, the thickness of the layer measured in the vertical direction of the figure, i.e. perpendicular to the running direction in width and to the running direction in length is uniform or substantially uniform over the transverse dimension of each resilient or reinforcing zone. However, as may be seen in the same figure, the thickness of the resilient zones varies increasingly and then decreasingly, passing via a maximum between its two joints with the reinforcing zones, but the thicknesses of the resilient film(s) and of the reinforcing zone(s) are such that in the region of their respective joint, the upper and/or lower surfaces of the layer are substantially without rough edges or discontinuity.

Thus, for example, the resilient film(s) have a grammage of approximately 10 to 25% greater than that of the reinforcing film(s), the resilient film(s) having, for example, a grammage of 55 g/m$^2$, whilst the reinforcing film(s) have a grammage of 45 g/m$^2$.

Figure 22:
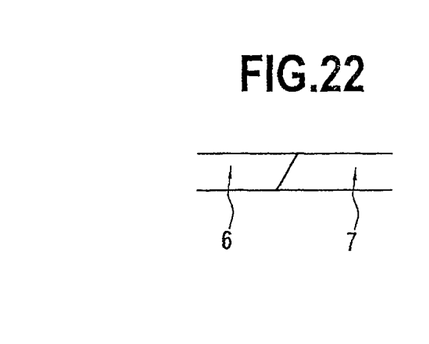
FIG. 22 shows a part of the view of FIG. 21 of a layer having a resilient film—reinforcing film interface produced in the form of a bevel.

Over the joint or connecting section, which extends over a width in general ranging between 3 and 10 mm, in particular 5 mm, the thickness of each (reinforcing and resilient) film is less than the thickness of the film beyond the joint. Thus, each film of the joint comprises a part of smaller thickness which is assembled by superposing onto the part of smaller thickness of the other film of the joint. The superposition creates in this manner in the region of the interface between the two films, as shown in FIG. 21, a type of step. Also it might be possible for the interface to be shaped in the form of a bevel, as shown in FIG. 22.

It may, however, occur in practice in the region of the interface connections between the two thermoplastic and resilient or elastomeric materials, that small bulges are formed due to the fact that the total thickness of the terminal parts which are superposed is slightly greater than the thicknesses of the two films on both sides of the joint.

In the present invention, by the term "film or resilient zone" in a given direction is understood a film or a zone which substantially returns to its initial shape after having been stretched or elongated in the given direction, at ambient temperature. Preferably, it is a film or a zone which only maintains a small amount of residual deformation or set after deformation and relaxation (permanent set or SET), namely less than 10%, more preferably less than 5% of the initial length, for an elongation of 100% of the initial length of the sample, at ambient temperature (T~23° C.).

More preferably, the resilient film is capable of being subjected to elongation at rupture of at least 300% at ambient temperature and preferably elongation of at least 600% and more preferably at least 1000% at ambient temperature and for a stretching speed of 508 mm/min. The material of which the resilient film is made may be either a pure elastomer, or mixtures having an elastomeric phase or a material which still has substantially elastomeric properties at ambient temperature, such as for example polyolefins from a metallocene-type catalysis. It may also comprise a thermoplastic material filler to assist, amongst other things, the formation of the integral layer with the reinforcing films.

Figure 4:
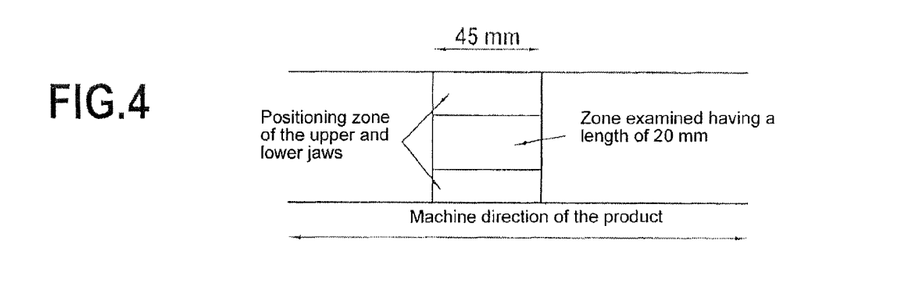
FIG. 4 is a diagram showing a sample of resilient or elastomeric material which has been prepared to determine the SET thereof.
Figure 5:
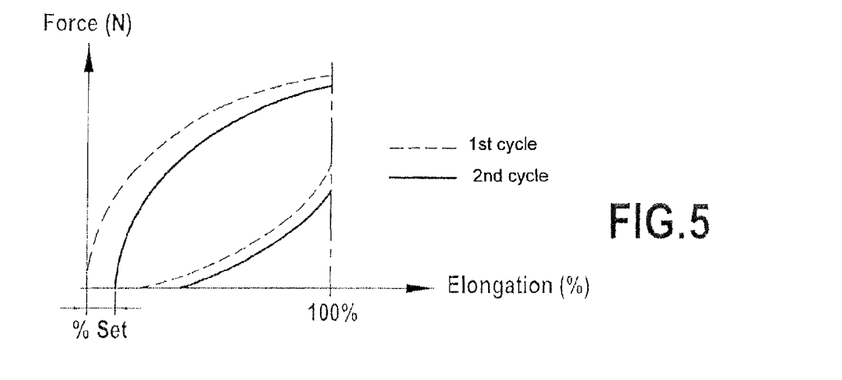
FIG. 5 shows the shape of the hysteresis curve obtained when determining the SET of a material which is, in particular, resilient or elastomeric.

To measure the remanence or SET of a sample, and thus to determine if it is a sample of a resilient element, in particular a film, the following method is used:

the sample is conditioned in a normal atmosphere, as defined in the ASTDM 5170 standard, at a temperature of 23° C.±2° C. and relative humidity of 50%±5%.
a dynamometer in accordance with the EN 10002 standard is used as equipment, in particular the Synergie 200H, 1 column, available from MTS Systems Corp. USA, in conjunction with TESTWORKS 4.04B utilisation software.
the sample is prepared by cutting out using a cutter the product of which it is desired to measure the resilience in a sample of rectangular shape (for example having a 45 mm width in the MD direction (machine direction perpendicular to the plane of FIG. 1) and a length in the CD direction (transverse direction, horizontal direction to FIG. 1) of 60 mm).
the sample is positioned between the jaws on both sides of the zone of which it is desired to test the resilience and on each side as shown schematically in FIG. 4;

The parameters are selected as follows:
Distance between jaws: 20 mm
Machine speed: 254 mm/min
Number of cycles: 2
Elongation of the product: 100% at constant speed The product is stretched at 100% by vertical displacement of the jaws, after the application of an initial load in the order of 0.05 N, then held in position for 30 seconds (first cycle), then allowed to return to the initial position where it is left for 60 seconds, then it is stretched again at 100%, held for 30 seconds (second cycle) and returned to the initial position. Thus the curve is obtained where the stretching force in N is a function of the elongation in %, said curve exhibiting a hysteresis, which may thus be characterised by the SET (n=2), namely the point of the curve at the start of the second cycle which intersects the X axis (elongation in %) in FIG. 5.

More preferably, the resilient film is capable of being subjected to elongation at rupture of at least 300% at ambient temperature and, preferably, an elongation of at least 600%, and more preferably of at least 1000% at ambient temperature and for a stretching speed of 508 mm/min. The material in which the resilient film may be made is either a pure elastomer, or mixtures having an elastomeric phase or a material which still has substantially elastomeric properties at ambient temperature, such as for example polyolefins from a metallocene-type catalysis. It may also comprise a thermoplastic material filler in order, amongst other things, to assist the formation of the integral layer with the reinforcing films.

The material of the resilient film which is, in particular, elastomeric may be a resilient material which is thermo-retractable or non-thermo-retractable. It may be formed, in particular, from polymers, such as copolymers of different types of monomer motif, for example alternating, such as A-B, or in sequence, for example A-A-A-B-B-B or statistical, for example A-A-B-A-B-B-A-A-A-B-A, of which the total network obtained may have different structures, either linear of the A-B-A type or radial of the A-B type, index n (n>2), or diblock of the A-B type, which are elastomeric, for example styrene/isoprene (SI) styrene/isoprene/styrene (SIS), styrene/butadiene/styrene (SBS), styrene-ethylene/butylene-styrene (SEBS), styrene-ethylene/propylene-styrene (SEPS) or SIBS copolymers. Mixtures of these elastomers with one another or with non-elastomers modifying specific characteristics other than the resilience may also be considered. For example, up to 50% by weight but preferably less than 30% by weight of polymer may be added as a stiffening additive, such as styrene polyvinyls, polystyrenes or poly α-methyl-styrene, epoxy polyesters, polyolefins, for example polyethylenes or certain ethylene/vinyl acetates, preferably those of a high molecular weight.

The material for the resilient film may be, in particular, a styrene-isoprene-styrene available, for example, from Kraton Polymers under the trade name KRATON D (registered trademark) or from DEXCO POLYMERS LP under the trade name VECTOR SBC 4211 (registered trademark). It is also possible to use a thermoplastic elastomer of polyurethane, in particular PELLATHANE (registered trademark) 2102-75A from The Dow Chemical Company. It is also possible to use a styrene-butadiene-styrene, in particular KRATON D-2122 (registered trademark) from Kraton Polymers, or VECTOR SBC 4461 (registered trademark) from Dexco Polymers LP. It is also possible to use a styrene-ethylene-butylene, in particular KRATON G-2832 (registered trademark) from Kraton Polymers, or a styrene-ethylene-butylene-styrene (SEBS) sequenced copolymer, in particular KRATON (registered trademark) G2703. It is also possible to use a copolymer of isooctyl acrylate and acrylic acid in accordance with the monomer ratios of 90/10. It is also possible to use a polyether polyamide sequenced copolymer PEBAX (registered trademark) 2533 from Arkema.

Other possible materials are polyolefin polymers having the characteristics of elastomers, in particular from metallocene catalysis, such as VISTAMAXX VM-1120 (registered trademark), available from Exxon Mobil Chemical or EPDM charged polymers of the Santoprene type.

In the case where glue is used as adhesive to fix the resilient films and the thermoplastic films to the non-woven fabrics, and possibly the non-woven fabrics to one another, it is possible according to the invention to use a glue such as non-reactive hot-melt glues, for example H2511 from Bostick, or a reactive glue, in particular AX75E from Bostick, or reactive PU glues.

Preferably, said glues have a chemical nature which is similar or compatible with a material forming the resilient film and/or the thermoplastic or reinforcing film as disclosed above.

Concerning the non-woven fabrics, it is possible to use non-woven fabrics of the spunbond and/or meltblown and/or calendered carded and/or spunlace type and having as base material one or more polyolefins, preferably polypropylene, polyester or a mixture thereof. In particular, the non-woven "spunbond" fabric, is based on long fibres or filaments, having a dTex count (mass in grams divided by a length of 10000 m of thread) of between 1 dTex and 6 dTex, for example 2.2 dTex. In particular, when the laminate comprises two layers of non-woven fabric, the layers may be of different types and/or of different materials.

Preferably, the or at least one of the non-woven fabrics or the two non-woven fabrics has (have) a grammage of between 5 and 25 g/m$^2$, in particular between 5 and 15 gm$^2$, more particularly between 5 and 10 g/m$^2$.

In particular, when the non-woven fabric is a non-woven fabric which does not have an inherent capacity to be stretched and has to be activated, the grammage is between 5 and 20 g/m$^2$, in particular approximately 15 g/m$^2$ for a spunbond or approximately 8 g/m$^2$ for a meltblown. When the non-woven fabric does not have to be activated for the laminate to have a resilient capacity, i.e. when the non-woven fabric has the inherent capacity to be stretched over an elongation range of at least up to 50%, preferably at least 100%, the grammage is preferably between 15 and 25 g/m$^2$, for example 22 g/m$^2$, for a calendered carded non-woven or 25 g/m$^2$ for a spunlace. Moreover, it is noteworthy that the two non-woven fabrics, in the case where there are two, may be different from one another.

To determine if an element, in particular a film, is more stretchable than another element, for example another film, according to the invention, it is possible to use a test of elongation under force until rupture as follows:

A dynamometer in accordance with the EN 10002 standard, is used as equipment, for example the same as for the resilience test above, namely the Synergie 200H, 1 column, available from MTS systems Corp, USA, in conjunction with TESTWORKS 4.04 B utilisation software. The rectangular-shaped sample is prepared, for example having a 45 mm width and a length of 60 mm. The sample is positioned between the jaws on both sides of the zone of which it is desired to test the elongation and on each side, as shown schematically in FIG. 4. The parameters are selected as follows:

Distance between jaws: 20 mm
Machine speed: 254 mm/min
Elongation of product: until rupture at constant speed.

Figure 23:
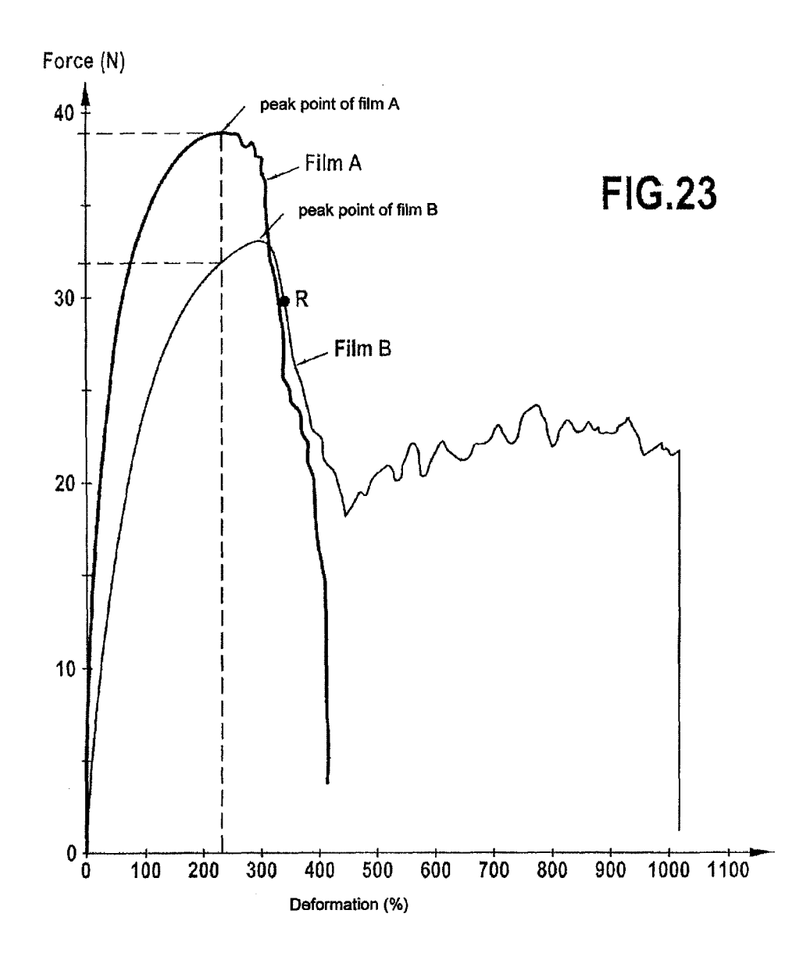
FIG. 23 shows examples of curves providing the stretching as a function of the force for testing the relative stretchable quality.

After having applied an initial load of 0.05 N, the product is stretched until rupture by vertical displacement of the jaws. Thus for each sample the characteristic curve is obtained where the stretching force in N is a function of the elongation in %, as shown in FIG. 23. Each curve comprises a peak point, from where the elongation increases with decreasing force. This peak corresponds to the transition to the state of destruction of the element.

To determine which of two elements, in particular of two films, is the least stretchable, by the above method the two elements are tested, in particular the two films, so as to obtain their respective characteristic curve. Each curve has a given peak point, to which a respective given elongation corresponds. Thus as reference elongation the smallest of the two given elongations of the two curves is selected or the given elongation in the case where the two given elongations are identical and for this given elongation, which is the smallest, the two stretching forces of each curve are compared and the element having for this reference elongation the greatest stretching force is the least stretchable element. Thus, for example in FIG. 23, the reference elongation is the elongation corresponding to the peak point of the film A, namely approximately 240% and at this reference elongation, the curve of the film A provides a stretching force of approximately 40 N and the curve of the film B provides a stretching force of approximately 32.5 N, so that it is the film A which is the least stretchable.

Concerning the material of the reinforcing strips, it is possible to select a material or a mixture of a plurality of materials such as those of the group of thermoplastics, for example polyethylene, polypropylene, polyester or any similar material, in addition to materials of the group of thermoplastic elastomers used for the resilient film (but of such a type that the reinforcing film has in all cases less elongation than the resilient film) which makes it possible to provide good compatibility of the materials forming the integral layer. Preferably a thermoplastic material is selected which has good compatibility with the resilient or elastomeric material of the resilient film so that the connection therebetween along their respective edge, after cooling, is the strongest possible connection. Specific examples of material, for the reinforcing films are Riblene MV 10 (trademark) polyethylene from Polimeri Europa or MG 9621 from Boréalis, or LD259 or LD655 from Exxon Mobil Chemical.

Layers of glue 10 and 11 are provided between the intermediate layer 4 consisting of the sections 5, 6, 7, 8 and 9. The strips of glue 10 and 11 are continuous at the interface between each non-woven fabric and each reinforcing strip and consist of strips of glue separated from one another by zones in the form of strips without glue between the non-woven fabrics and the resilient films. However, it might also be possible not to bond continuously the reinforcing films and the non-woven fabrics, for example by also producing in this region separate strips of glue, or even spot gluing or gluing by random spraying. The reinforcing strips and the resilient films are arranged between the two non-woven fabrics by co-extrusion. They are each assembled by co-extrusion, so that in the co-extrusion equipment they come into contact along their respective lateral edges 12, 13, 14 and 17, in a softened material state and under pressure. The close contact of the two edges of the two softened materials with one another of the resilient strips and of the reinforcing strips has the result that the two materials are joined to one another in the equipment and maintain this joint after cooling. Thus, for example, the resilient film may be based on a thermoplastic elastomer, whilst the reinforcing strips may be thermoplastic, which ensures mutual fixing of the two interfaces on the lateral edges in a simple manner.

Figure 2:
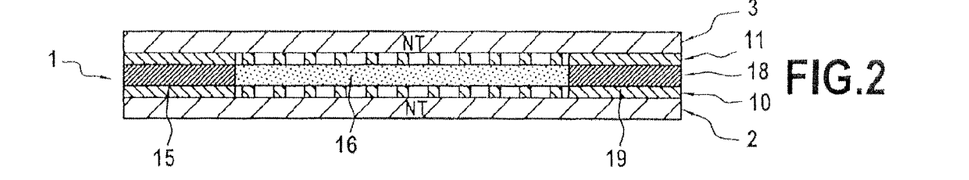
FIG. 2 shows a schematic cross-sectional view of a further embodiment of a laminate according to the invention.

In FIG. 2, a further embodiment is shown in which the laminate comprises a film 18 formed by a central resilient film 16 and two lateral reinforcing strips (15, 19). In this embodiment, instead of a central reinforcing strip there is a single resilient film. The other features of the laminate of FIG. 2 are identical to that disclosed for the laminate of FIG. 1.

Figure 3:
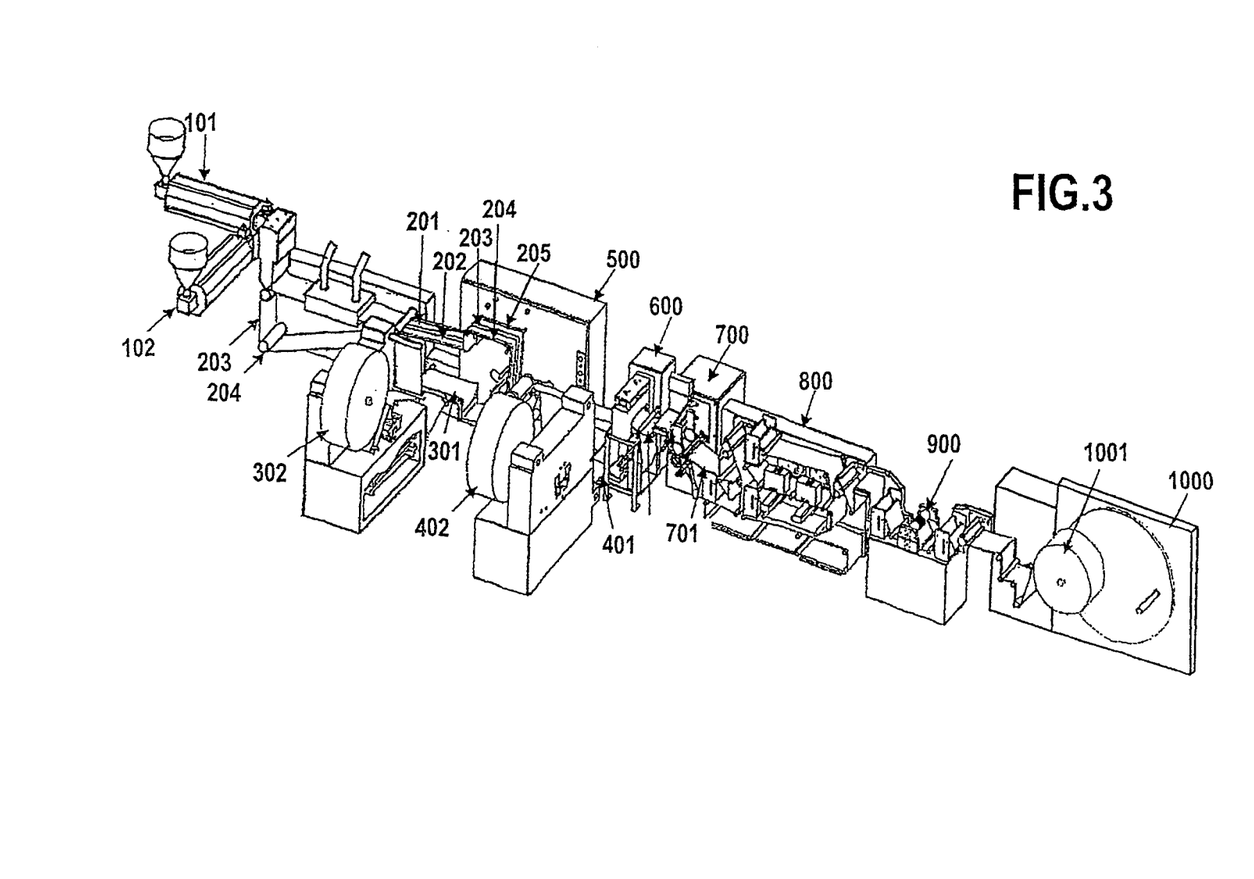
FIG. 3 shows a perspective view of an installation for producing a laminate according to the invention, in particular of the laminates of FIGS. 1 and 2.

In FIG. 3, an installation for producing a laminate is shown according to the invention: the installation comprises an extruder 101 which forms by extrusion two webs 201, 202 of resilient films which by means of systems using belts 203 and rollers 204 are transported between two drums at the same time as two layers of non-woven fabric 301 and 401 to be fixed by cooling of the elastomeric material between the non-woven fabrics in a fixing unit 500. The non-woven fabric 301 is unwound from a bobbin 302. The second non-woven fabric 401 is unwound from a bobbin 402. Three webs 203, 204, 205 of thermoplastic material are also formed by the extruder 102. The five webs 201 to 205 are co-extruded adjacent to one another with their edges contiguous so that at the outlet of the co-extrusion equipment and subsequently after cooling, they form a single piece. The composite consisting of the non-woven fabrics 301 and 401 and resilient and thermoplastic webs 201 to 205, is namely the composite 601 and is then laminated in a calendering machine 600, cut to the correct width in a cutting system 700 across the width comprising circular blades 701, then passed into a welding unit 800, enabling welding of the longitudinal edges. The non-woven fabrics are finally activated by defibrillation in an activation unit 900.

At the outlet of the activation unit 900, the entire laminate is wound onto a winding machine 1000 into a roll 1001 which is then directly moved to the units for manufacturing the nappies, for depositing onto a nappy.

Preferably, the resilient or elastomeric film(s) have a thickness of between 20 microns and 120 microns. Similarly, the reinforcing strips have preferably the same thickness.

Depending on the application, it is possible to select the dimensions of the reinforcing films made of thermoplastic material, so that one thereof extends exactly as far as one of the left or right edges of the laminate, whilst at the other edge, either the strip also extends as far as the right or left edge exactly, or protrudes by a short distance to the outside beyond the edge of the laminate, or in contrast terminates set back from this edge so as to form a small edge, in particular without reinforcing film.

Figure 6:
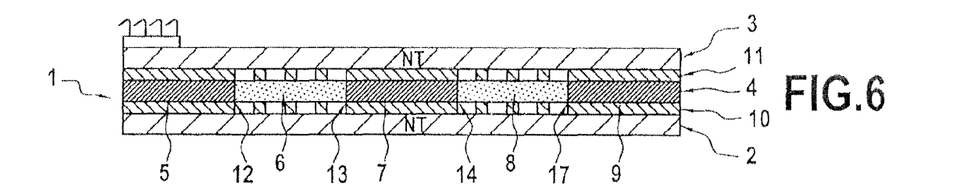
FIG. 6 shows a further embodiment of a laminate according to the invention which corresponds to the laminate of FIG. 1 to which an element comprising hooks has been added on the top.

In FIG. 6, the laminate of FIG. 1 is shown to which has been fixed on the upper non-woven fabric, in the zone opposite or corresponding to the left reinforcing strip, a hook sheet made of thermoplastic material, consisting of a strip made of thermoplastic material from which protrude hooking elements, in particular hooks. The width of this hook strip is less than the width of the reinforcing strip. It is also possible to provide such a strip on top of one or all the other reinforcing strips of the embodiments of FIGS. 1 and 2, depending on the selected application. The fixing of this hook strip or these hook strips may be made by adhesive, glue or welding, in particular ultrasonic welding.

In the examples disclosed above, two layers of identical non-woven fabrics have been used. It is also possible to provide two layers made of different non-woven fabric materials or having different grammages and it is also possible to provide a single layer of non-woven fabric instead of two.

In the examples disclosed above, reinforcing films have been extruded from the same extruder 102. It is also possible to provide a third extruder to extrude one of the zones with a formulation consisting of thermoplastic material which is different from the other reinforcing zone.

In the above examples, the layer 4 comprises two resilient films and three reinforcing films. It is also possible to provide that this layer is composed of a plurality of resilient and reinforcing zones with in each case a number greater than or equal to 4.

Furthermore, it is possible to provide the addition of colorants, in masterbatch form, in liquid form or in powder form, up to 7%, preferably less than 1%, in the formulation of the resilient film(s) and/or of the reinforcing film(s) so that they are easily distinguishable.

Similarly, the formulation of each film is made according to the rules of the prior art by extrusion and possibly incorporates agents of the "processing aid", swelling, anti UV, antiblock type, etc.

In FIGS. 7 to 20, further embodiments of a laminate according to the invention are shown in which relative to the embodiments of FIGS. 1 and 2, the number and/or the widths of the layers of non-woven fabric, the number of resilient films, the number of reinforcing films, the widths of the reinforcing films, the relative positioning of the reinforcing films with regard to the edges of the laminate, and the positioning of an element comprising hooks have been varied. Naturally, also contained in the present description are the embodiments obtained by combining two or more of the embodiments of FIGS. 1, 2, 6 to 18, in particular when one or more features which are not found in a different disclosed embodiment are taken from one of these embodiments and that this or these features of said one embodiment is or are added to said different embodiment. In these figures, the same reference numerals have been used as in FIGS. 1 and 2 to describe identical elements.

Figure 7:
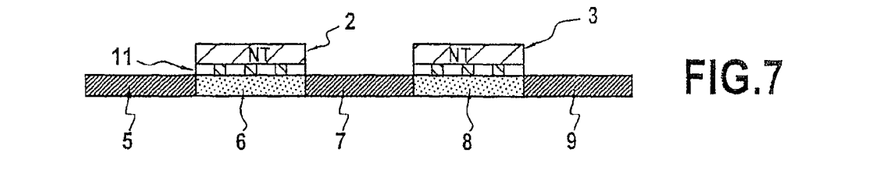
FIGS. 7 to 20 show further possible embodiments of a laminate according to the invention.

In FIG. 7, a laminate is disclosed which only comprises an upper layer of non-woven fabric, and which only extends over the two resilient films 6 and 8. The layer 4 comprises three reinforcing films 5, 7 and 9 and two resilient films 6 and 8.

Figure 8:
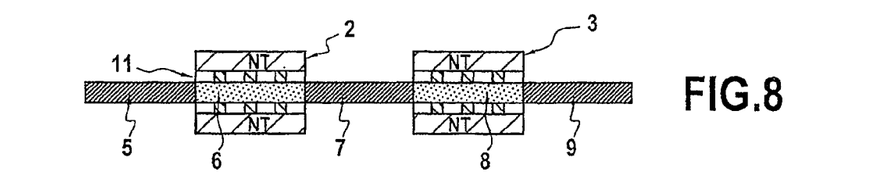

In FIG. 8, an embodiment is shown which is substantially identical to that of FIG. 7, with the exception that it also comprises a lower layer of non-woven fabric, which also only extends on the resilient films.

Figure 9:
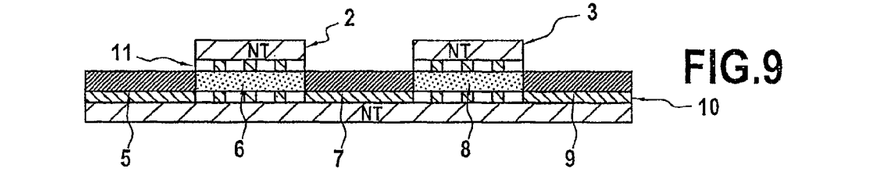

In FIG. 9, a further embodiment is shown which is substantially identical to that of FIG. 7, with the exception that a lower layer of non-woven fabric has been added which extends over the entire width of the intermediate layer, exactly from one edge to the other edge of this layer.

Figure 10:
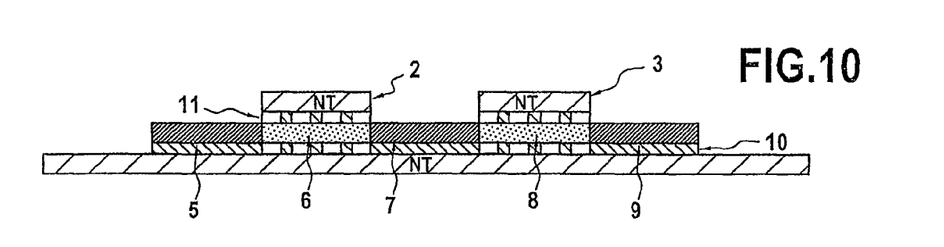

In FIG. 10, an embodiment is shown which is substantially identical to that of FIG. 9, with the exception that the lower non-woven fabric extends beyond the lateral edges of the intermediate layer.

Figure 11:
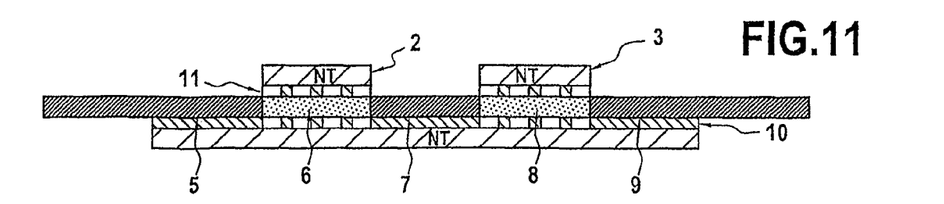

In FIG. 11, an embodiment is shown which is substantially identical to that of FIG. 9, with the exception that the lower non-woven fabric extends on this side of the lateral edges of the intermediate layer, the two terminal reinforcing films protruding laterally beyond the two lower and upper non-woven fabrics.

Figure 12:
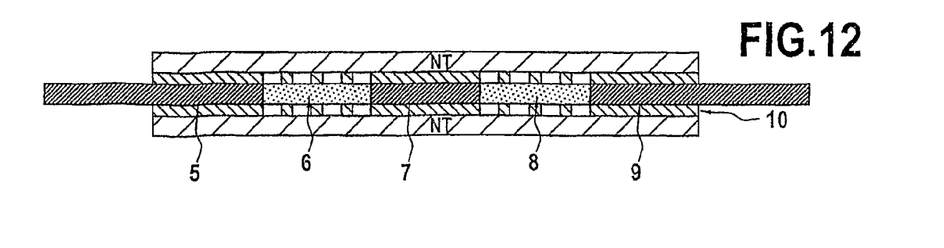

In FIG. 12, an embodiment is shown which is substantially identical to that of FIG. 1, with the exception that the two terminal reinforcing films protrude laterally beyond the two lower and upper non-woven fabrics.

Figure 13:
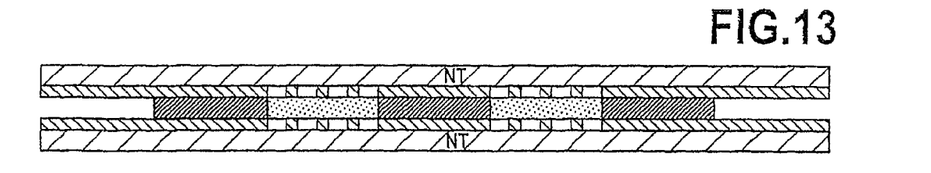

In FIG. 13, an embodiment is shown which is substantially identical to that of FIG. 1, with the exception that the two terminal reinforcing films do not extend as far as the lateral edges of the laminate, remaining laterally set back relative to the two non-woven fabrics.

Figure 14:
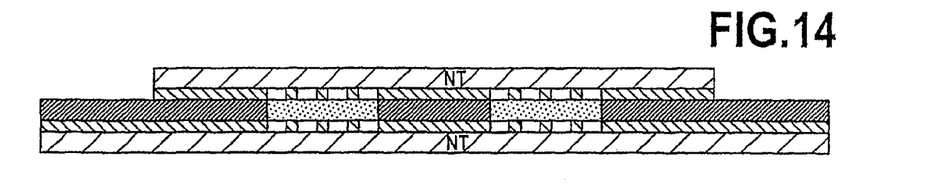

In FIG. 14, an embodiment is shown which is substantially identical to that of FIG. 1, with the exception that the upper layer of non-woven fabric does not extend as far as the terminal edges of the intermediate layer, the two reinforcing films and the lower layer of non-woven fabric extending laterally beyond the upper layer of non-woven fabric.

Figure 15:
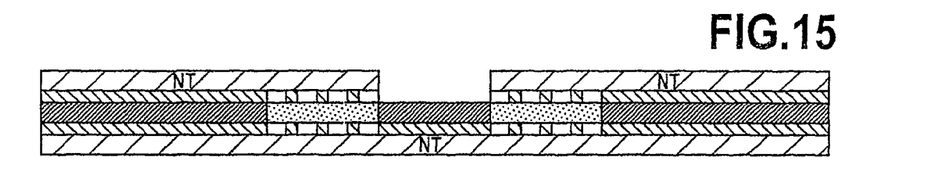
Figure 18:
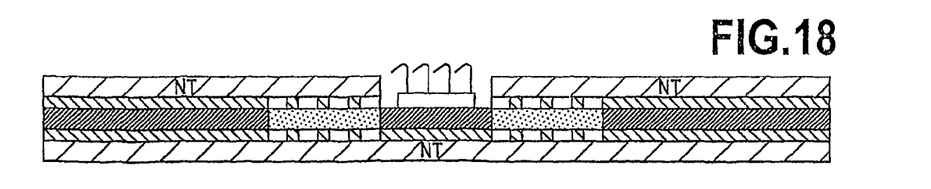

In FIG. 15, an embodiment is shown which is substantially identical to that of FIG. 1, with the exception that the upper layer of non-woven fabric does not extend over the central film, leaving said central film exposed, an exposed surface which may be used for the direct fixing of an element comprising hooks as shown in FIG. 18.

Figure 16:
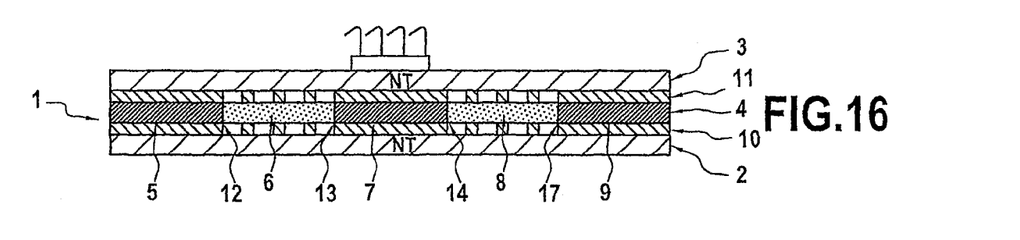

In FIG. 16, an embodiment is shown which is identical to that of FIG. 6, with the exception that the element comprising hooks is fixed to the upper non-woven fabric in the region of the central film and not in the region of one of the terminal reinforcing films.

Figure 17:
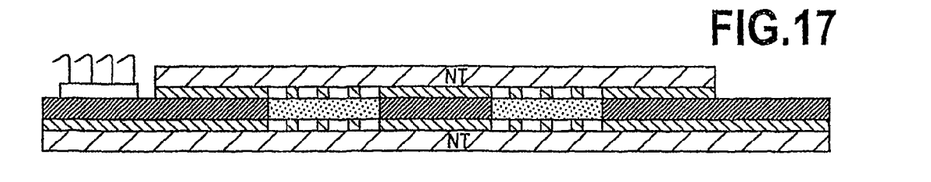

In FIG. 17, an embodiment of FIG. 14 is shown in which an element comprising hooks has been fixed to a terminal part of the terminal reinforcing film, which protrudes beyond the upper layer of non-woven fabric.

In FIG. 18, the embodiment of FIG. 15 is shown in which an element comprising hooks has been fixed to the part left exposed of the central film.

Figure 19:
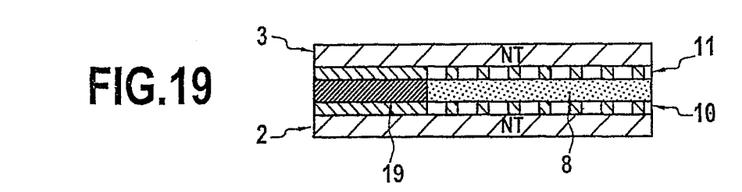

In FIG. 19, a laminate is shown which comprises only one resilient film and only one terminal reinforcing film. The reinforcing film extends from the resilient film as far as the lateral edge (to the left in the figure). The terminal edge of the reinforcing film on the side opposing said one resilient film is the location of the points of the terminal reinforcing film which are the most remote of any resilient film.

Figure 20:
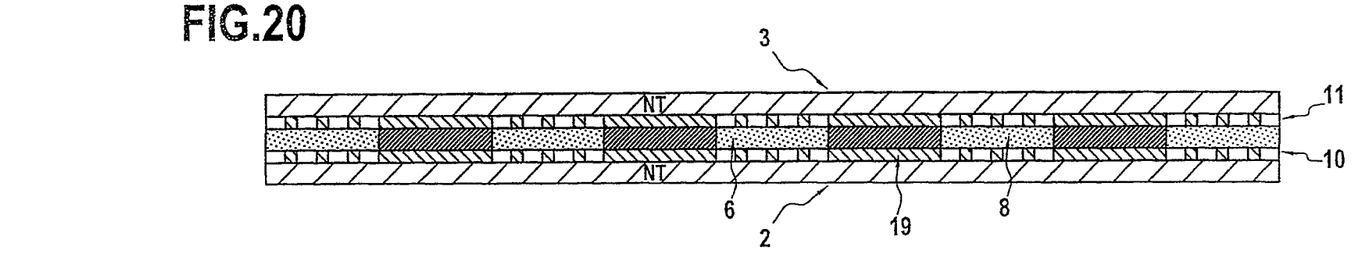

In FIG. 20, a laminate is shown in which the layer alternately comprises five reinforcing films and four resilient films.

Figure 24:
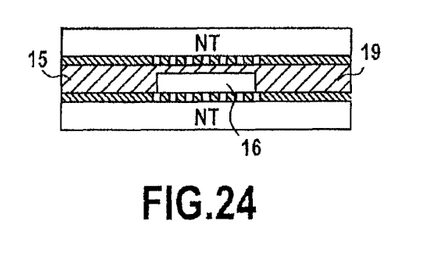
FIG. 24 shows a further embodiment of a laminate according to the invention.
Figure 27:
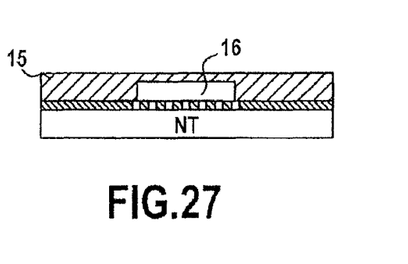
FIG. 27 shows a further embodiment of a laminate according to the invention.

In FIG. 24, an embodiment of a laminate is shown according to the invention, comprising an upper layer of non-woven fabric and a lower layer of non-woven fabric. The intermediate layer comprises, in succession and co-extruded together, a reinforcing film, a resilient film and a reinforcing film. During the extrusion, the two reinforcing films have the tendency to protrude over the resilient film until a small thin layer is formed over the resilient film, the thin layer made of reinforcing material (less stretchable than the elastomeric material) connecting the two reinforcing films. The thin layer is sufficiently thin relative to the thickness of resilient material, however, for the layer to preserve its resilient character in the region of the resilient film. The thin layer is in direct contact (solely by the interposition of glue) with the upper non-woven fabric. On the lower side, there is direct contact between the elastomeric film and the lower non-woven fabric (solely by the interposition of points or lines of glue) and between the reinforcing films and the lower non-woven fabric. In FIG. 27, a variant of the embodiment of the laminate of FIG. 24 is shown, the laminate of FIG. 27 being identical to the laminate of FIG. 24 with the exception that it does not comprise the upper layer of non-woven fabric and the intermediate layer of glue between the co-extruded layer and the upper layer of non-woven fabric. Thus, the upper surface of this laminate of FIG. 27 is formed solely from the material forming the reinforcing strip and the bridge part above the resilient layer, with possibly a hook strip fixed to this upper surface.

Figure 25:
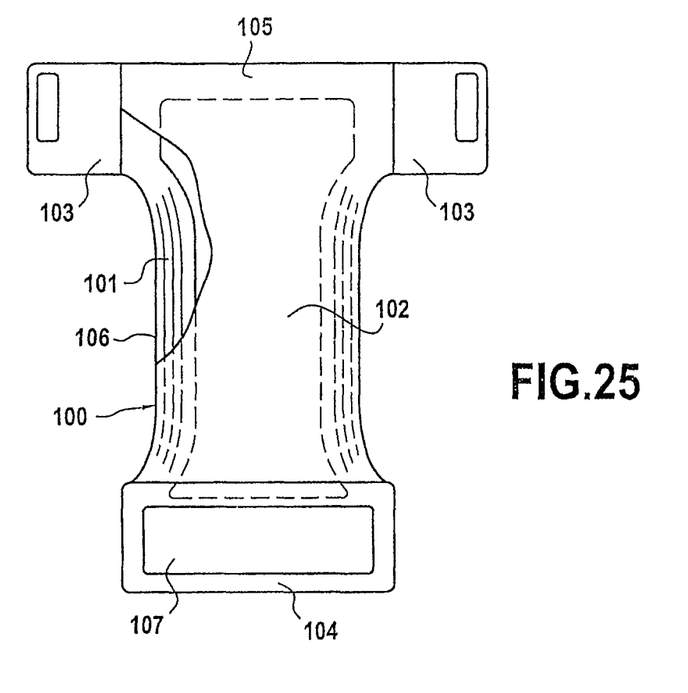
FIG. 25 shows an embodiment of a nappy according to the invention incorporating a fastening wing or tab comprising hooks and incorporating a laminate as disclosed in the preceding figures.

In FIG. 25, a nappy is shown arranged substantially flat and not closed up onto itself. The layer 100 consists of a structure formed by a stacked arrangement of an impermeable external covering 101 and a liner 102 on the side of the body, permeable to body fluids. Between the covering and the liner an absorbent material is arranged.

The structure forms a front part 104, intended to be located on the front side of the wearer of the nappy when it is worn, a rear part 105, intended to be located on the rear side of the wearer of the nappy when it is worn, and a crotch part 106, connecting the rear and front parts. On the front part, on the external face of the external covering 101, has been arranged for example by bonding, ultrasonic welding or the like, a loop part 107, for example in the form of a looped knitted fabric, a looped woven fabric or a looped non-woven fabric.

From the two opposing edges of the rear part of the structure protrude the intermediate hook parts 103 consisting of one of the laminates disclosed above to which have been fixed hooks intended to cooperate with the loops from the front part to close the nappy around the waist of the wearer. In particular, the hooks are fixed in the region of one of the reinforcing strips, either directly on top, or with the interposition of the layer of non-woven fabric located above the reinforcing strip.

The intermediate parts 103 are joined to the rear part on the two sides thereof, preferably, as shown, substantially in the upper region of the rear part. This joining may be carried out directly or indirectly. For example, it is possible to fix directly each intermediate part to the rear part by the use of adhesive, thermal or ultrasonic welding and the like. It is also possible to provide an intermediate part assisting this joining or even that the intermediate 103 parts are produced in one piece or integrally with the rear part. The fixing of each intermediate part to the upper lateral edges of the rear part of the structure of the nappy is carried out in the region of the reinforcing strip or one of the reinforcing strips of the laminate forming this intermediate part, either directly or with the interposition of the layer of non-woven fabric located above this reinforcing strip, the presence of this reinforcing strip facilitating this fixing.

Figure 26:
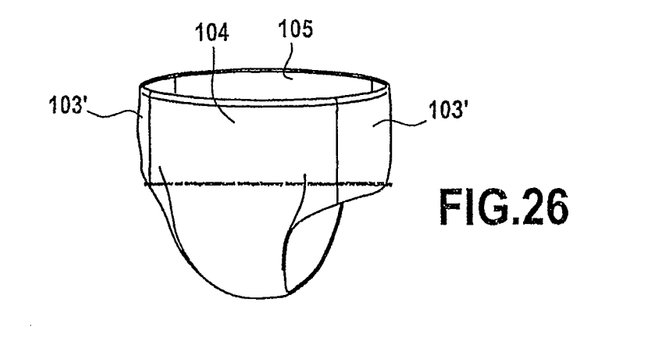
FIG. 26 shows in a perspective view a further embodiment of a nappy according to the invention.

In FIG. 26, a further embodiment of a nappy according to the invention is shown. In this embodiment, the intermediate parts 103' are joined both to the rear part (as in the embodiment of FIG. 25) and the front part 104' in a manner similar to the manner in which the rear and intermediate parts are joined. The intermediate parts are, as in the embodiment of FIG. 25, also formed by one of the laminates disclosed above. The only difference is that in this embodiment the intermediate part 103' does not comprises hooks and the join with the front part is not detachable as is the case in the embodiment of FIG. 25 by the cooperation of the hooks and loops. Thus, in this embodiment of FIG. 26, it is not necessary to provide a loop part in the front part. The fixing of each intermediate part to the lateral upper edges of the rear part and the front part of the structure of the nappy is carried out in the region of one respective reinforcing strip of the laminate forming this intermediate part, either directly or with the interposition of the layer of non-woven fabric located above this reinforcing strip, the presence of the reinforcing strips facilitating this fixing.

The invention claimed is:

1. Hook part of a self-gripping hook and loop closure, in particular for a nappy, comprising a hook element comprising a sheet from which hooks protrude and a laminated element fixed to the hook element, the laminate extending in a transverse direction between two respective left and right lateral edges, comprising a layer fixed to at least one layer of non-woven fabric by a layer of adhesive, in particular interposed between two layers of non-woven fabric by being fixed by one respective layer of adhesive to each layer of non-woven fabric, the layer being a single layer comprising a resilient zone in the form of film, in particular made of an elastomeric material, characterized in that:
   the single layer comprises at least one terminal reinforcing zone in the form of film which extends from the resilient zone in the form of film towards one of the lateral edges;
   no resilient zone being located between said one of the lateral edges and the reinforcing zone in the form of film; and
   the at least one reinforcing zone in the form of film being less stretchable than said resilient zone in the form of film, in particular being less resilient, and preferably being non-resilient, for example being made of a thermoplastic material.

2. Hook part according to claim 1, characterized in that the layer comprises two terminal reinforcing zones in the form of films on both sides of said one resilient zone in the form of film.

3. Hook part according to claim 1, characterized in that the layer is interposed between two layers or sheets of non-woven fabric and fixed respectively by one respective layer of adhesive to each layer or sheet of non-woven fabric.

4. Hook part according to claim 1, characterized in that the integral layer comprises a second resilient zone in the form of film at a distance from said resilient zone in the form of film and, outside the two terminal reinforcing zones, a central zone in the form of film extending between said one resilient zone in the form of film and the second resilient zone in the form of film.

5. Hook part according to claim 1, characterized in that the thicknesses of the resilient films(s) and of the reinforcing zone(s) are such that in the region of their respective joint, the upper and/or lower surfaces of the layer are substantially without rough edges or discontinuity.

6. Hook part according to claim 5, characterized in that in the region of the joints the two films each have a thickness which is smaller than in the vicinity of the joint, the total thicknesses of the two films in the region of the joint being substantially equal to the thickness of one or other of the films in the vicinity of the joint.

7. Hook part according to claim 6, characterized in that the joint between two resilient and reinforcing zones is formed in the region of the joint along an interface in the form of a bevel.

8. Hook part according to claim 1, characterized in that the hook element is fixed on an external face of the laminate, to a zone which is located in the region of one of the terminal reinforcing zones, in the form of film(s).

9. Hook part according to claim 1, characterized in that the at least one of the layers of non-woven fabrics has a grammage ranging between 5 and 15 g/m².

10. Method for obtaining a hook part according to claim 1, characterized in that the zones in the form of reinforcing films and the zone(s) in the form of resilient film(s) are formed by co-extrusion so that in the co-extrusion equipment the materials forming the zones in the form of films come into contact along their respective lateral edges in a softened material state and under pressure so that the reinforcing zone(s) in the form of film(s) and the resilient zone(s) in the form of film(s) form a single layer at the outlet of the co-extrusion equipment and maintain this assembly after cooling.

11. Nappy comprising a self-gripping closure having a loop part and a hook part according to claim 1, each fixed or attached to the nappy so as to cooperate with one another to close the nappy, in particular in the region of the waistband of the nappy.

\* \* \* \* \*

UNITED STATES PATENT AND TRADEMARK OFFICE
CERTIFICATE OF CORRECTION

PATENT NO. : 8,998,874 B2
APPLICATION NO. : 13/258047
DATED : April 7, 2015
INVENTOR(S) : Thierry Marche and Nathalie Moinard It is certified that error appears in the above-identified patent and that said Letters Patent is hereby corrected as shown below:

In the Claims

Column 14, line 34, Claim 4 - delete the word "integral"

Signed and Sealed this
Eighth Day of September, 2015

Michelle K. Lee
*Director of the United States Patent and Trademark Office*